(12) United States Patent
Kleiner et al.

(10) Patent No.: US 10,631,778 B2
(45) Date of Patent: Apr. 28, 2020

(54) PATIENT SETUP USING RESPIRATORY GATED AND TIME RESOLVED IMAGE DATA

(71) Applicant: Varian Medical Systems International AG, Cham (CH)

(72) Inventors: David Kleiner, Mellingen (CH); Patrik Kunz, Baden (CH); Michael Huber, Beinwil am See (CH)

(73) Assignee: Varian Medical Systems International AG (CH)

( * ) Notice: Subject to any disclaimer, the term of this patent is extended or adjusted under 35 U.S.C. 154(b) by 743 days.

(21) Appl. No.: 14/873,184

(22) Filed: Oct. 1, 2015

(65) Prior Publication Data

US 2017/0095197 A1 Apr. 6, 2017

(51) Int. Cl.
*G06T 7/00* (2017.01)
*A61B 6/00* (2006.01)
(Continued)

(52) U.S. Cl.
CPC .......... *A61B 5/4836* (2013.01); *A61B 5/0071* (2013.01); *A61B 5/055* (2013.01); *A61B 5/08* (2013.01); *A61B 6/032* (2013.01); *A61B 6/037* (2013.01); *A61B 6/463* (2013.01); *A61B 6/486* (2013.01); *A61B 6/487* (2013.01); *A61B 6/5223* (2013.01); *A61B 6/5235* (2013.01); *A61N 5/1037* (2013.01); *A61N 5/1068* (2013.01); *G06T 7/0012* (2013.01); *A61B 6/5288* (2013.01); *A61B 6/541* (2013.01); *A61N 2005/1061* (2013.01);
(Continued)

(58) Field of Classification Search
None
See application file for complete search history.

(56) References Cited

U.S. PATENT DOCUMENTS

| 2005/0180544 A1 | 8/2005 | Sauer et al. |
| 2006/0291621 A1 | 12/2006 | Yan et al. |
| (Continued) | | |

OTHER PUBLICATIONS

Partial European Search Report dated Mar. 1, 2017, for corresponding EP Patent Application No. 16190309.1, 9 pages.
(Continued)

*Primary Examiner* — Matthew C Bella
*Assistant Examiner* — Brian D Shin
(74) *Attorney, Agent, or Firm* — Vista IP Law Group, LLP

(57) ABSTRACT

A method for patient setup includes: obtaining a first two-dimensional movie having a first plurality of image frames; obtaining a first plurality of two-dimensional images; and displaying the first plurality of two-dimensional images together with the image frames from the first two-dimensional movie in an overlay configuration and in a synchronized manner, wherein the act of displaying is performed during a patient setup procedure. A method for patient setup includes: obtaining a plurality of three-dimensional images; obtaining a first two-dimensional movie having a first plurality of image frames; determining a first plurality of two-dimensional images from the plurality of three-dimensional images; and displaying the first plurality of two-dimensional images together with the image frames from the first two-dimensional movie in an overlay configuration and in a synchronized manner, wherein the act of displaying is performed during a patient setup procedure.

52 Claims, 7 Drawing Sheets

(51) Int. Cl.

| | | |
|---|---|---|
| *A61N 5/10* | (2006.01) | |
| *A61B 5/00* | (2006.01) | |
| *A61B 5/055* | (2006.01) | |
| *A61B 5/08* | (2006.01) | |
| *A61B 6/03* | (2006.01) | |

(52) U.S. Cl.
CPC ............... *G06T 2207/10081* (2013.01); *G06T 2207/10088* (2013.01); *G06T 2207/10104* (2013.01); *G06T 2207/10121* (2013.01)

(56) References Cited

U.S. PATENT DOCUMENTS

| | | |
|---|---|---|
| 2007/0270689 A1 | 11/2007 | Lothert |
| 2008/0031404 A1 | 2/2008 | Khamene et al. |
| 2012/0051515 A1 | 3/2012 | Brown |

OTHER PUBLICATIONS

Mengjiao, Wang et al., "2D/4D marker-free tumor tracking using 4D CBCT as the reference image," Physics in Medicine and Biology, Institute of Physics Publishing, Bristol GB, vol. 59, No. 9, Apr. 8, 2014.

Chen, Ting et al., "Objected constrained registration and manifold learning: A new patient setup approach in image guided radiation therapy of thoracic cancer," Medical Physics, AIP, Melville, NY, US, vol. 40, No. 4, Apr. 1, 2013.

Xu, Qianyi, et al., "Registration of on-board X-ray images with 4DCT: A proposed method of phase and setup verification for gated radiotherapy," Physica Medica, dated Oct. 9, 2009, pp. 117-125 (9 pages).

T Chen, et al., Abstract for "Real Time Tumor Motion Monitoring during IGRT based on Manifold Learning and Dynamic Registration between 4DCT and Fluoroscopy," Med. Phys. 37, 3098 (2010), 1 page.

Extended European Search Report dated Jun. 26, 2017, for corresponding EP Patent Application No. 16190309.1, 15 pages.

a)

b)

c)

PATIENT SETUP USING RESPIRATORY GATED AND TIME RESOLVED IMAGE DATA

FIELD

The field of the application relates to medical procedures, and more particularly, to systems and methods for setting up patient in medical procedures.

BACKGROUND

Radiation therapy involves medical procedures that selectively expose certain areas of a human body, such as cancerous tumors, to high doses of radiation. Radiation may also be used to obtain images of the patient during an imaging procedure.

In a radiation treatment procedure, before radiation is delivered, the patient is first setup at the treatment machine. Currently, image guidance is used to correctly setup the patient at the treatment machine, with respect to the planned position. In one technique, one or multiple x-ray projection images of the patient are acquired and registered to a two-dimensional digitally reconstructed radiographs (DRR), calculated for the corresponding x-ray projection direction and geometry using the diagnostic computer tomography (CT) three-dimensional image. The result of this rigid registration is then used to calculate a couch position correction. The couch position correction is then used to adjust the patient position until the patient position matches the planned position In some cases, instead of using two-dimensional image projections for the patient setup procedure, a CT image of the patient may be acquired, and a three-dimensional rigid registration to the planning CT image may be performed.

SUMMARY

A method for patient setup includes: obtaining a plurality of three-dimensional images; obtaining a first two-dimensional movie having a first plurality of image frames; determining a first plurality of two-dimensional images from the plurality of three-dimensional images; and displaying the first plurality of two-dimensional images together with the image frames from the first two-dimensional movie in an overlay configuration and in a synchronized manner, wherein the act of displaying is performed during a patient setup procedure. As used in this specification, the term "patient setup procedure", or any of other similar terms, refers to any procedure that is performed while treatment radiation is not being delivered. By means of non-limiting examples, the patient setup procedure may be a process that involves determining and/or adjusting a position of a target relative to a treatment device, a patient position verification process, an imaging process, an image processing process, etc., or any combination of the foregoing. Thus, a patient setup procedure may or may not involve a patient.

Optionally, the method further includes: obtaining a second two-dimensional movie having a second plurality of image frames; determining a second plurality of two-dimensional images from the plurality of three-dimensional images; and displaying the second plurality of two-dimensional images together with the image frames from the second two-dimensional movie in an overlay configuration and in a synchronized manner.

Optionally, the first plurality of image frames in the first two-dimensional movie comprises a first set of fluoroscopic images, and the second plurality of image frames in the second two-dimensional movie comprises a second set of fluoroscopic images.

Optionally, the first set of fluoroscopic images comprises kV images, and the second set of fluoroscopic images comprises MV images.

Optionally, the first set of fluoroscopic images comprises a first set of kV or MV images, and the second set of fluoroscopic images comprises a second set of kV or MV images.

Optionally, the act of determining the plurality of two-dimensional images comprises determining a cross section in one of the three-dimensional images that matches with one of the image frames in the first two-dimensional movie, wherein the match results in a first registration.

Optionally, the act of determining the plurality of two-dimensional images further comprises: applying the first registration for an other one of the image frames in the first two-dimensional movie; wherein the one of the image frames is associated with a first phase of a respiratory cycle, the other one of the image frames is associated with a second phase of the respiratory cycle, the first phase being different from the second phase.

Optionally, the act of determining the plurality of two-dimensional images comprises determining an other cross section in an other one of the three-dimensional images that matches with an other one of the image frames in the first two-dimensional movie, wherein the one of the image frames is associated with a first phase of a respiratory cycle, the other one of the image frames is associated with a second phase of the respiratory cycle, the first phase being different from the second phase.

Optionally, the first plurality of two-dimensional images and the image frames from the first two-dimensional movie are synchronized to a common time frame based on breathing signals provided from a breathing monitoring device.

Optionally, the three-dimensional images are binned into a first number of phase bins, and wherein the method further comprises binning the first plurality of image frames in the first two-dimensional movie into a second number of phase bins, the first number being equal to the second number.

Optionally, a phase bin in the second number of phase bins has multiple images from the first plurality of image frames, and wherein the method further comprises selecting one of the images from the phase bin in the second number of the phase bins for registration with one of the three-dimensional images.

Optionally, the selected one of the images has an associated breathing phase that is closer to a breathing phase associated with the one of the three-dimensional images compared to other ones of the images.

Optionally, the first two-dimensional movie is generated using x-ray.

Optionally, the x-ray comprises kV x-ray.

Optionally, the x-ray comprises MV x-ray.

Optionally, the first two-dimensional movie is generated using ultrasound or magnetic resonance.

Optionally, the three dimensional images comprise CBCT images, magnetic resonance images, CT images, or PET images.

Optionally, the first plurality of two-dimensional images has a first frame rate, the first two-dimensional movie has a second frame rate, the first frame rate being different from the second frame rate.

Optionally, the overlay configuration indicates whether a target is at a desired position for receiving treatment radiation.

An apparatus for patient setup includes: a processing unit having one or more input for obtaining a plurality of three-dimensional images, and for obtaining a first two-dimensional movie having a first plurality of image frames; wherein the processing unit comprises a two-dimensional image determination module configured for determining a first plurality of two-dimensional images from the plurality of three-dimensional images; and wherein the processing unit further comprises a synchronization display module configured to output the first plurality of two-dimensional images and the image frames from the first two-dimensional movie for display together in an overlay configuration and in a synchronized manner in a patient setup procedure.

Optionally, the one or more input of the processing unit is configured for obtaining a second two-dimensional movie having a second plurality of image frames; wherein the two-dimensional image determination module is configured for determining a second plurality of two-dimensional images from the plurality of three-dimensional images; and wherein the synchronization display module is configured for displaying the second plurality of two-dimensional images together with the image frames from the second two-dimensional movie in an overlay configuration and in a synchronized manner.

Optionally, the first plurality of image frames in the first two-dimensional movie comprises a first set of fluoroscopic images, and the second plurality of image frames in the second two-dimensional movie comprises a second set of fluoroscopic images.

Optionally, the first set of fluoroscopic images comprises kV images, and the second set of fluoroscopic images comprises MV images.

Optionally, the first set of fluoroscopic images comprises a first set of kV or MV images, and the second set of fluoroscopic images comprises a second set of kV or MV images.

Optionally, the two-dimensional image determination module is configured for determining a cross section in one of the three-dimensional images that matches with one of the image frames in the first two-dimensional movie, wherein the match results in a first registration.

Optionally, the two-dimensional image determination module is configured for applying the first registration for an other one of the image frames in the first two-dimensional movie; wherein one of the image frames is associated with a first phase of a respiratory cycle, the other one of the image frames is associated with a second phase of the respiratory cycle, the first phase being different from the second phase.

Optionally, the two-dimensional image determination module is configured for determining an other cross section in an other one of the three-dimensional images that matches with an other one of the image frames in the first two-dimensional movie; wherein the one of the image frames is associated with a first phase of a respiratory cycle, the other one of the image frames is associated with a second phase of the respiratory cycle, the first phase being different from the second phase.

Optionally, the processing unit is also configured to obtain breathing signals generated using a breathing monitoring device, and wherein the synchronization display module is configured to synchronize the first plurality of two-dimensional images and the image frames from the first two-dimensional movie to a common time frame based on the breathing signals.

Optionally, the three-dimensional images are binned into a first number of phase bins, and wherein the processing unit comprises a binning module configured to bin the first plurality of image frames in the first two-dimensional movie into a second number of phase bins, the first number being equal to the second number.

Optionally, a phase bin in the second number of phase bins has multiple images from the first plurality of image frames, and wherein the two-dimensional image determination module is configured for selecting one of the images from the phase bin in the second number of phase bins for registration with one of the three-dimensional images.

Optionally, the selected one of the images has an associated breathing phase that is closer to a breathing phase associated with the one of the three-dimensional images compared to other ones of the images.

Optionally, the first two-dimensional movie is generated using x-ray.

Optionally, the x-ray comprises kV x-ray.

Optionally, the x-ray comprises MV x-ray.

Optionally, the first two-dimensional movie is generated using ultrasound or magnetic resonance.

Optionally, the three dimensional images comprise CBCT images, magnetic resonance images, CT images, or PET images.

Optionally, the first plurality of two-dimensional images has a first frame rate, the first two-dimensional movie has a second frame rate, the first frame rate being different from the second frame rate.

Optionally, the overlay configuration indicates whether a target is at a desired position for receiving treatment radiation.

A processor-program product includes a set of instruction, an execution of which by a processing unit causes a method of detecting camera defect to be performed, the method comprising: obtaining a plurality of three-dimensional images; obtaining a first two-dimensional movie having a first plurality of image frames; determining a first plurality of two-dimensional images from the plurality of three-dimensional images; and displaying the first plurality of two-dimensional images together with the image frames from the first two-dimensional movie in an overlay configuration and in a synchronized manner, wherein the act of displaying is performed during a patient setup procedure.

A method for patient setup includes: obtaining a first two-dimensional movie having a first plurality of image frames; obtaining a first plurality of two-dimensional images; and displaying the first plurality of two-dimensional images together with the image frames from the first two-dimensional movie in an overlay configuration and in a synchronized manner, wherein the act of displaying is performed during a patient setup procedure.

Optionally, the two-dimensional images are two-dimensional sections of respective three-dimensional images.

Optionally, the first plurality of two-dimensional images comprises a first plurality of projection images.

Optionally, the overlay configuration indicates whether a target is at a desired position for receiving treatment radiation.

An apparatus for patient setup includes: a processing unit configured to obtain a first two-dimensional movie having a first plurality of image frames, and to obtain a first plurality of two-dimensional images; wherein the processing unit comprises a synchronization display module configured to output the first plurality of two-dimensional images and with the image frames from the first two-dimensional movie for display in an overlay configuration and in a synchronized manner in a patient setup procedure.

Optionally, the two-dimensional images are two-dimensional sections of respective three-dimensional images.

Optionally, the first plurality of two-dimensional images comprises a first plurality of projection images.

Optionally, the overlay configuration indicates whether a target is at a desired position for receiving treatment radiation.

A processor-program product includes a set of instruction, an execution of which by a processing unit causes a method of detecting camera defect to be performed, the method comprising: obtaining a first two-dimensional movie having a first plurality of image frames; obtaining a first plurality of two-dimensional images; and displaying the first plurality of two-dimensional images together with the image frames from the first two-dimensional movie in an overlay configuration and in a synchronized manner, wherein the act of displaying is performed during a patient setup procedure.

Other and further aspects and features will be evident from reading the following detailed description.

DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only exemplary embodiments and are not therefore to be considered limiting in the scope of the claims.

DETAILED DESCRIPTION

Figure 1:
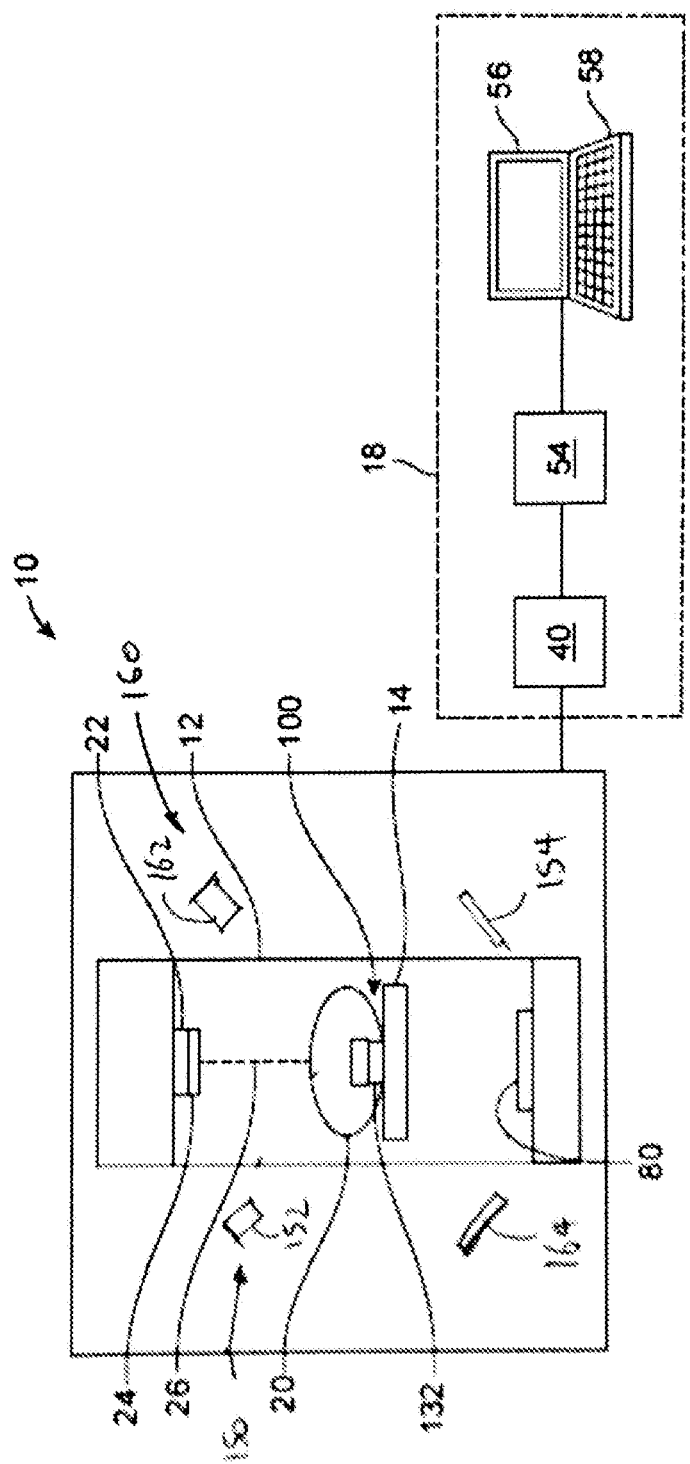
FIG. 1 illustrates a radiation treatment system.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1 illustrates a radiation treatment system 10. The system 10 includes an arm gantry 12, a patient support 14 for supporting a patient 20, and a control system 18 for controlling an operation of the gantry 12 and delivery of radiation. The system 10 also includes a radiation source 22 that projects a beam 26 of radiation towards the patient 20 while the patient 20 is supported on support 14, and a collimator system 24 for changing a cross sectional shape of the radiation beam 26. The radiation source 22 may be configured to generate a cone beam, a fan beam, or other types of radiation beams in different embodiments. Also, in other embodiments, the source 22 may be configured to generate proton beam as a form of radiation for treatment purpose. Also, in other embodiments, the system 10 may have other form and/or configuration. For example, in other embodiments, instead of an arm gantry 12, the system 10 may have a ring gantry 12.

In the illustrated embodiments, the radiation source 22 is a treatment radiation source for providing treatment energy. In other embodiments, in addition to being a treatment radiation source, the radiation source 22 can also be a diagnostic radiation source for providing diagnostic energy for imaging purpose. In such cases, the system 10 will include an imager, such as the imager 80, located at an operative position relative to the source 22 (e.g., under the support 14). In further embodiments, the radiation source 22 may be a treatment radiation source for providing treatment energy, wherein the treatment energy may be used to obtain images. In such cases, in order to obtain imaging using treatment energies, the imager 80 is configured to generate images in response to radiation having treatment energies (e.g., MV imager). In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 22 is able to generate X-ray radiation at a plurality of photon energy levels within a range anywhere between approximately 10 keV and approximately 20 MeV. In the illustrated embodiments, the radiation source 22 is carried by the arm gantry 12. Alternatively, the radiation source 22 may be located within a bore (e.g., coupled to a ring gantry).

In the illustrated embodiments, the control system 18 includes a processing unit 54, such as a processor, coupled to a control 40. The control system 18 may also include a monitor 56 for displaying data and an input device 58, such as a keyboard or a mouse, for inputting data. The operation of the radiation source 22 and the gantry 12 are controlled by the control 40, which provides power and timing signals to the radiation source 22, and controls a rotational speed and position of the gantry 12, based on signals received from the processing unit 54. Although the control 40 is shown as a separate component from the gantry 12 and the processing unit 54, in alternative embodiments, the control 40 can be a part of the gantry 12 or the processing unit 54.

In some embodiments, the system 10 may be a treatment system configured to deliver treatment radiation beam towards the patient 20 at different gantry angles. During a treatment procedure, the source 22 rotates around the patient 20 and delivers treatment radiation beam from different gantry angles towards the patient 20. While the source 22 is at different gantry angles, the collimator 24 is operated to change the shape of the beam to correspond with a shape of the target tissue structure. For example, the collimator 24 may be operated so that the shape of the beam is similar to a cross sectional shape of the target tissue structure. In another example, the collimator 24 may be operated so that different portions of the target tissue structure receive different amount of radiation (as in an IMRT procedure).

As shown in FIG. 1, the medical system 10 also includes a first imaging system 150 and a second imaging system 160. In the illustrated embodiments, the first imaging system 150 is a first fluoroscopic imaging system having a first x-ray source 152 and a corresponding first detector 154. Similarly, the second imaging system 160 is a second fluoroscopic imaging system having a second x-ray source 162 and a corresponding second detector 164. The first and second imaging systems 150, 160 may be used to generate x-ray movies for use to setup patient. In some embodiments, the two imaging systems 150, 160 may be oriented at 90° with respect to each other. In other embodiments, the two imaging systems 150, 160 may be oriented at other angles with respect to each other. The imaging systems 150, 160 may be coupled to a same gantry ring that allows them to rotate together, or to separate respective gantry rings that allow them to rotate independently. Also, in some embodiments, the first and second imaging systems 150, 160 may be configured to generate images simultaneously together to form respective first and second x-ray movies. In other embodiments, the first and second imaging systems 150, 160 may be configured to operate in an interleaving or staggering manner, so that only one of the two imaging systems 150, 160 is activated at a time. In further embodiments, the medical system 10 may include a single imaging system (e.g., imaging system 150). In such cases, the imaging system may be operated to obtain the first and second x-ray movies sequentially.

In a radiation treatment procedure, before treatment radiation is delivered to the patient 20, the patient 20 is first setup at the medical system 10. In accordance with one or more embodiments described herein, respiratory motion of the patient 20 is taken into account when performing patient setup. In one technique, one or multiple fluoroscopic x-ray movie(s) are acquired at the medical system 10. The x-ray movie(s) is then registered to a time resolved three-dimensional CT data. In some cases, a patient monitoring device may be provided to determine breathing phases of the patient 20. For example, respiration monitoring system RPM available at Varian in Palo Alto, Calif., may be used. The breathing phases may be used to synchronize the fluoroscopic x-ray movie(s) with the three-dimensional CT data. Also, cross sections (two-dimensional images) of the three-dimensional images corresponding to the image frames in the fluoroscopic x-ray movies may be obtained. Since the three-dimensional images are synchronized with the fluoroscopic x-ray movie, the two-dimensional images derived from the three-dimensional images are also synchronized with the fluoroscopic x-ray movie. The synchronized movie(s) and the two-dimensional images derived from the three-dimensional CT images may be displayed together in an overlay configuration. This allows a physician to see any deviation in the tissue position between the fluoroscopic x-ray movie and the cross sections of the three dimensional images through the different breathing phases of the patient during the patient setup procedure.

Figure 2:
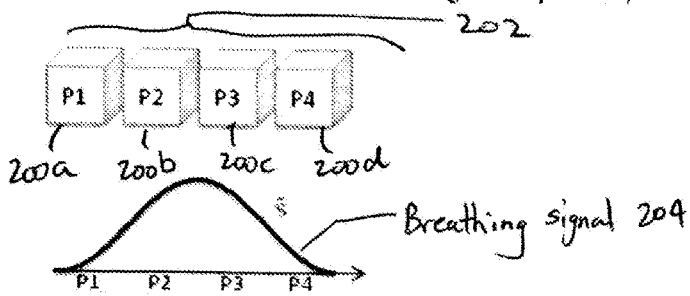
FIG. 2 illustrates time-resolved image data.
Figure 2:
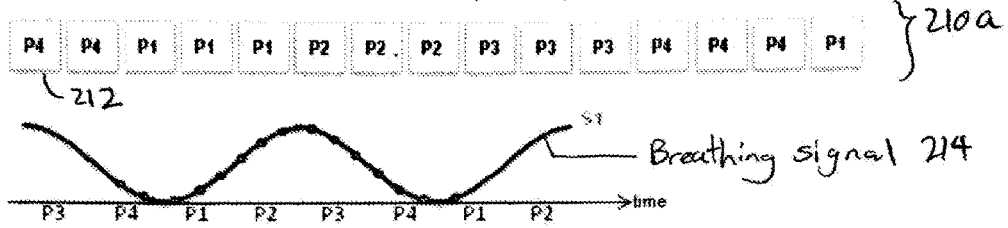
Figure 2:
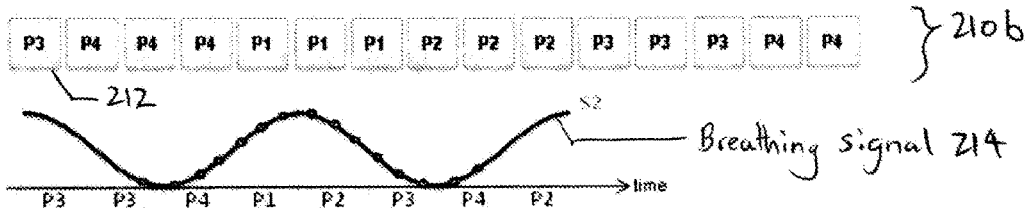

FIG. 2 illustrates examples of image data that may be used to perform patient setup. As shown in the figure, the patient setup technique involves a plurality of three-dimensional images 200a-200d. The three-dimensional images 200a-200d may be arranged in a sequence so that they form a video 202. As shown in the figure, the three-dimensional images 200a-200d are associated with four respective breathing phase ranges P1-P4 of a respiratory cycle. If a respiratory cycle has phases quantified from 0°-360°, then the first phase range P1 may cover 0°-90°, the second phase range P2 may cover 90°-180°, the third phase range P3 may cover 180°-270°, and the fourth phase range may cover 270°-360°. In one implementation, the three-dimensional images 200a-200d may be volumetric CT images that are generated using a CT machine during treatment planning. In particular, projection images may be obtained at different gantry angles by rotating a diagnostic radiation source around the patient during treatment planning. As the projection images are being obtained, breathing signals 204 representing a breathing of the patient are being obtained. Such may be accomplished using a breathing monitoring device. The breathing signals 204 may be processed to determine the different breathing phases. After the projection images are obtained, projection images may be grouped into different phase ranges or phase bins. For example, if a breathing cycle of the patient is divided into four ranges P1-P4, like that shown in FIG. 2, then projection images with corresponding breathing phases that fall within each phase range is grouped together in that phase bin. After that, the projection images in each phase bin (e.g., phase bin for P1) are then used in a CT reconstruction process to reconstruct the three-dimensional image 200a. This is repeated for other phase bins to obtain other three-dimensional images 200b-200d.

In other embodiments, the respiratory cycle may be divided in a number of phase ranges or phase bins that are more or fewer than four. In such cases, the number of three-dimensional images 200 may correspondingly be more or fewer than four.

Also, in the illustrated embodiments, the three-dimensional images 200a-200d are volumetric CT images that are obtained during treatment planning. In other embodiments, the three-dimensional images 200a-200d may be volumetric CT images obtained during a patient setup procedure. The CT images may be cone beam CT (CBCT) in some cases. Also, in some embodiments, instead of CT images, the three-dimensional images 200a-200d may be positron emission tomography (PET) images. In further embodiments, the images 200 may be generated using other techniques, such as magnetic resonance imaging (MRI), in which cases, the images 200 may be MRI images.

As shown in FIG. 2, the patient setup technique described herein also involves a first two-dimensional movie 210a, and a second two-dimensional movie 210b. Each of the movies 210a, 201b includes a plurality of image frames 212 that are generated during the patient setup procedure. In the illustrated embodiments, the first two-dimensional movie 210a includes a plurality of fluoroscopic x-ray images generated using the first imaging system 150, and the second two-dimensional movie 210b includes a plurality of fluoroscopic x-ray images generated using the second imaging system 160. In other embodiments, instead of two two-dimensional movies 210a, 210b, the patient setup technique described herein may use only one two-dimensional movie, or more than two two-dimensional movies.

As shown in the figure, the frame rate of the two-dimensional movies 210a, 210b is different from the frame rate of the movie formed by the three-dimensional images 200a-200d. In particular, as shown in the example, there are four three-dimensional images 200a-200d in a respiratory cycle. However, there are ten image frames in a respiratory cycle in each of the movies 210a, 210b. Thus, the frame rate of the two-dimensional movies 210a, 210b is higher than that of the movie 202 formed by the three-dimensional images 200a-200d. In other embodiments, the frame rates may be the same. In further embodiments, the frame rate of the two-dimensional movies 210a, 210b may be lower than that of the movie 202 formed by the three-dimensional movies 200a-200d.

As shown in FIG. 2, while the fluoroscopic x-ray images 212 are generated, breathing signals 214 representing a breathing of the patient are again being obtained. Such may be accomplished using a breathing monitoring device. The breathing signals 214 may be processed to determine the different breathing phases. Also, the fluoroscopic x-ray images 212 in each movie 210 may be grouped into different phase ranges or phase bins, wherein the number of phase ranges or phase bins is the same number (e.g., 4 in the example) as that for the three-dimensional images 200. In the above example, there are four phase ranges P1-P4. Accordingly, the fluoroscopic x-ray images 212 in each movie 210 are binned into the four phase bins that correspond with the phase ranges P1-P4. Thus, through the breathing signals, the image frames 212 in the two-dimensional movie 210 may be registered with corresponding ones of the three-dimensional images 200.

Figure 3:
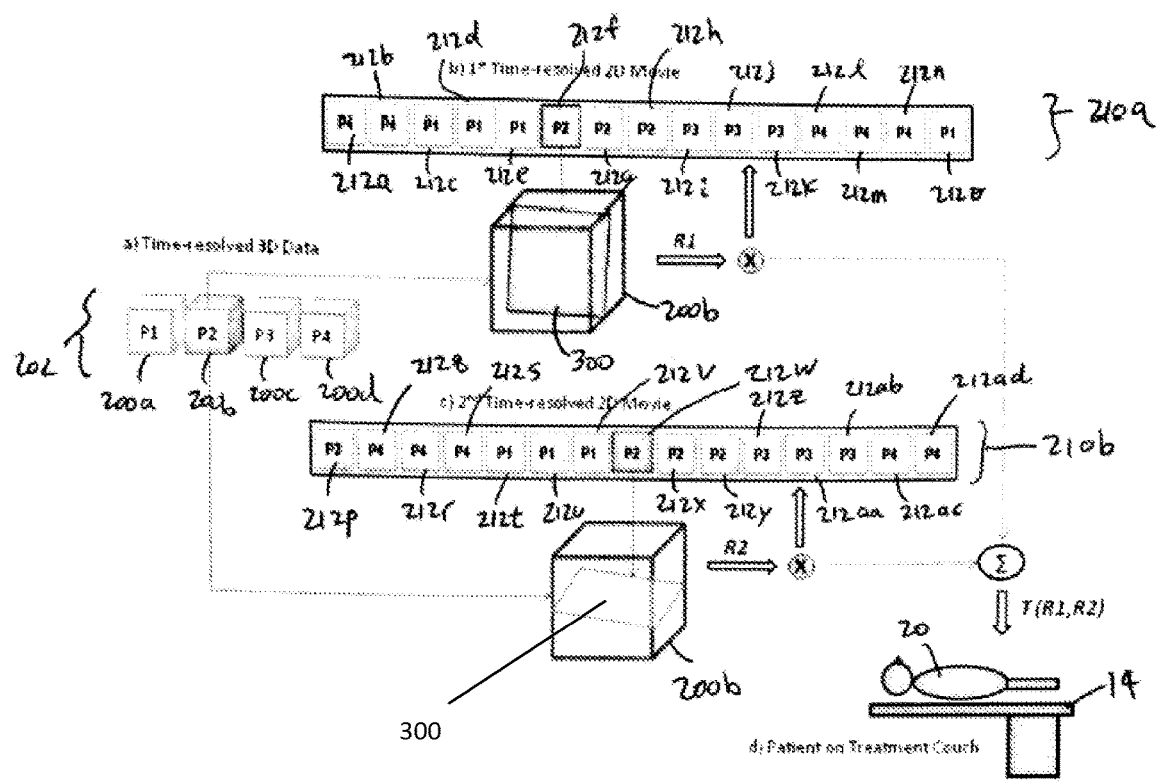
FIG. 3 graphically illustrates a technique for patient setup in accordance with some embodiments.

FIG. 3 graphically illustrates a patient setup technique in accordance with some embodiments. As shown in the figure, the three-dimensional images 200a-200d obtained from treatment planning are associated with respective phase ranges P1-P4. Also, as discussed, through breathing signals obtained from breathing monitoring device, the image frames 212 in the first two-dimensional movie 210a are associated with respective phase ranges P1-P4. Similarly, through breathing signals obtained from breathing monitoring device, the image frames 212 in the second two-dimensional movie 210b are associated with respective phase ranges P1-P4. Because the frame rate of the two-dimensional movie 210 may be higher than the frame rate of the three-dimensional movie 202, several consecutive image frames 212 may have the same associated phase range (e.g., P1) before the next phase range is reached.

In accordance with some embodiments, during patient setup, a processing unit may access the three-dimensional images 200a-200d, the image frames 212 in the first two-dimensional movie 210a, and the image frames 212 in the second two-dimensional movie 210b. In the example, the first two-dimensional movie 210a includes image frames 212a-212o. The processing unit may select an image frame 212 (image frame 212f with associated phase range P2) from the two-dimensional movie 210a, and may also select a corresponding three-dimensional image (three-dimensional image 200b in the example) with the same associated phase range (P2 in the example).

The processing unit may then determine a cross section 300 in the three-dimensional image 200b that matches with the selected image frame 212f. In one implementation, the processing unit may have a two-dimensional image determination module configured to determine the cross section 300 as the two-dimensional image that matches the selected image frame 212f. The two-dimensional image 300 may be displayed together with the image frame 212f in an overlay configuration for presentation to a physician.

The process of determining cross section 300 may be repeated for other image frames 212 in the first two-dimensional movie 210a. Thus, a cross section 300 from one of the three-dimensional images 200a-200d may be displayed in an overlay configuration with each of the image frames 212 in the first two-dimensional movie 210a. This will cause two movies to be displayed in an overlay configuration and in a synchronized manner.

As shown in the figure, from the match, the processing unit can determine a registration R1 (e.g., transformation matrix) that maps the selected image frame 212f to the cross section 300 in the three-dimensional image 200b. The registration R1 represents the orientation in the three-dimensional image 200b that corresponds with that of the image frame 212f in the first two-dimensional movie 210a. Since all of the image frames 212 in the first two-dimensional movie 210a are generated at the same orientation with respect to the patient 20, the same registration R1 may be used to determine cross sections 300 of other three-dimensional images 200 that match other image frames 212 in the two-dimensional movie 210a, including those with different associated phase ranges (e.g., P1, P3, P4). For example, the same registration R1 may be applied to the three-dimensional image 200b to obtain cross section 300. The resulting cross section 300 will be displayed together with the image frame 212g at another time point, and also displayed with image frame 212h at another time point (because they have the same corresponding breathing phase range P2). Similarly, the same registration R1 may be applied to the three-dimensional image 200c (with associated phase range P3) to obtain a cross section 300 from the image 200c. The resulting cross section 300 will be displayed together with image frame 212i at a time point, and also with image frame 212j at another time point, and also with image frame 212k at another time point (because they all have the same corresponding breathing phase range P3).

The above technique is advantageous because it allows a plurality of two-dimensional images 300 (derived from volumetric images 200) to be displayed together with image frames 212 from the first two-dimensional movie 210a in an overlay configuration and in a synchronized manner. From the overlay images, a physician in a patient setup procedure can see whether certain tissue is at the same position as that in the treatment planning through the different breathing phases of a breathing cycle. It is possible that certain tissue remains in the same position as that in the treatment planning for certain breathing phases, but falls outside a certain positional tolerance in another breathing phase. The above technique allows the physician to capture this deviation, which is not possible with pervious technique in which only one image is matched without considering the breathing of the patient.

In the above embodiments, the same registration R1 is used for determining the cross sections 300 of the three-dimensional images 200 for display with all image frames 212 in the two-dimensional movie 210a, regardless of the associated breathing phase ranges P1-P4. In other embodiments, the processing unit may determine four different cross sections 300 from the four respective three-dimensional images 200a-200d for the four respective phase ranges P1-P4. In such cases, when determining the cross section 300 from the three-dimensional image 200c for display with the image frames 212i-212k (having the same associated phase range P3), the processing unit find a cross section 300 from the three-dimensional image 300c that matches with image frame 212i. The same cross section 300 from the three-dimensional image 300c is also used for display with the image frame 212j, and also with image frame 212k.

In the illustrated embodiments, the same process described above may be performed for the second two-dimensional movie 210b, which includes image frames 212p-212ad. In particular, the processing unit may select an image frame 212 (image frame 212w with associated phase range P2) from the second two-dimensional movie 210b, and may also select a corresponding three-dimensional image (three-dimensional image 200b in the example) with the same associated phase range (P2 in the example). The processing unit may then determine a cross section 300 in the three-dimensional image 200b that matches with the selected image frame 212w. In one implementation, the processing unit may have a two-dimensional image determination module configured to determine the cross section 300 as the two-dimensional image that matches the selected image frame 212w. The two-dimensional image 300 may be displayed together with the image frame 212w in an overlay configuration for presentation to a physician. The process of determining cross section 300 may be repeated for other image frames 212 in the second two-dimensional movie 210b. Thus, a cross section 300 from one of the three-dimensional images 200a-200d may be displayed in an overlay configuration with each of the image frames 212 in the second two-dimensional movie 210b. This will cause two movies to be displayed in an overlay configuration and in a synchronized manner.

In some embodiments, the registrations R1 and R2 (which may be matrix transformations), may be used to obtain T(R1,R2), which is a transformation matrix that converts the two 2D/3D image registrations (R1-R2) into a physical couch correction with six degrees of freedom (e.g., pitch, roll, rot, lat, lng, vrt).

Figure 4A:
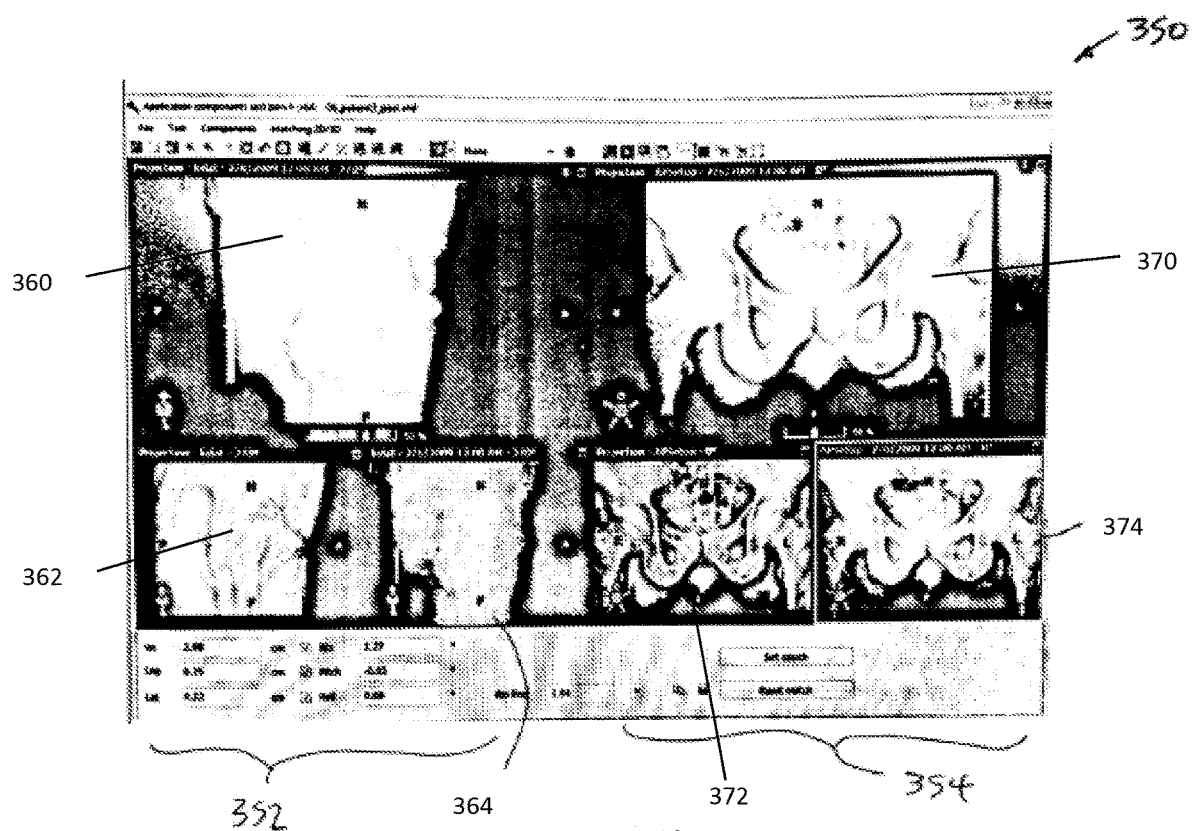
FIG. 4A illustrates an example of a display.
Figure 4B:
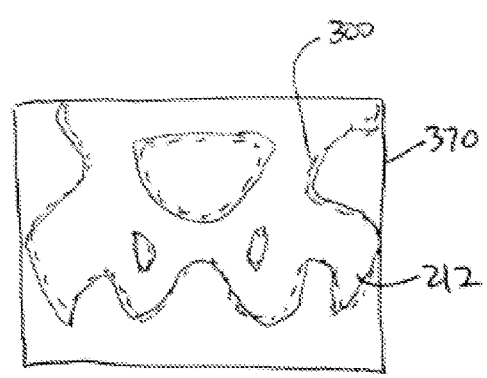
FIG. 4B illustrates one of the windows in the display of FIG. 4A.

FIG. 4A illustrates an example of a display 350, particularly showing a first display region 352, and a second display region 354. The first display region 352 includes a first window 360 sequentially displaying the image frames 212 from the first movie 210a together with two-dimensional images 300 derived from the three-dimensional images 200a-200d in an overlay configuration and synchronized manner, wherein for a certain given time instance, the same image frame 212 from the first movie 210a is also displayed in window 364, and the two-dimensional image 300 is also displayed in window 362. As shown in the figure, an image frame 212 from the first two-dimensional movie 210a is being displayed at a certain time point in an overlay configuration with a two-dimensional image 300 derived from one of the three-dimensional images 200a-200d. However, it should be understood that as time passes, different image frames 212 from the first two-dimensional movie 210a may be displayed in an overlay configuration with other two-dimensional images 300. Thus, two movies are displayed together in an overlay configuration and in a synchronized manner. Similarly, the second display region 354 includes a second window 370 displaying the image frames 212 from the second movie 210b together with two-dimensional images 300 derived from the three-dimensional images 200a-200d in an overlay configuration and synchronized manner, wherein for a certain given time instance, the same image frame 212 from the second movie 210b is also displayed in window 374, and the two-dimensional image 300 is also displayed in window 372. The image frame 212 and the two-dimensional image 300 in the window 370 are more clearly shown in FIG. 4B.

Since the first and second movies 210a, 210b are generated at different orientations with respect to the patient 20, by viewing both windows 360, 370, the physician can see whether certain tissue is where it should be for different breathing phases of the respiratory cycle, and from two different angles. If the tissue is within positional tolerance through the different phases of the breathing cycle, or through the important phases that matter, then treatment radiation may be delivered to treat the patient. On the other hand, if the tissue is not within positional tolerance at certain phase(s) of the breathing cycle, the physician may operate the treatment system 10 to re-position the patient 20. For example, the patient support 14 may be moved (e.g., translated and/or tilted). Alternatively, the physician may adjust the treatment plan based on the detected deviation. Also, by displaying the image frames 212 together with two-dimensional images 300 derived from the three-dimensional images 200 as two movies in an overlay configuration and synchronized manner, the physician can easily see whether anything in the human anatomy has changed since the treatment planning, whether the patient 20 is breathing the same way, and whether the relationship between certain fiducial position and tumor position is still the same as that determined in treatment planning.

Using the above new approach, patient setup is not based anymore on pure static image information, but allows considering as well respiratory induced tumor and organ motion. Also, the above approach involving respiratory synchronization and geometrical registration allows reduction in setup inaccuracies induced by respiratory motion and improves the image based registration. As another benefit, the above patient setup technique may be optimized for better targeting the tumor or sparing organs at risk. This improves the efficacy of the treatment and/or reduces dose induced side effects.

Also, in some embodiments, from the images presented in the display 350, variation of different target movements can be captured during the patient setup, so that the physician can determine whether the target is at a desired position (e.g., in sight of a treatment beam) or not.

In addition, in some embodiments, if a variation of a position of a target between the two overlayed images (e.g., an image frame 212 from the first movie 210a and a two-dimensional image 300 derived from one of the three-dimensional images 200a-200d) exceeds a certain threshold, such condition may be used to trigger an adjustment of a treatment plan. In one implementation, the processing unit may be configured to determine a difference in a position of a target (or a certain fiducial position) between an image frame 212 from the first movie 210a and a two-dimensional image 300 derived from one of the three-dimensional images 200a-200d. If the difference exceeds a certain threshold, then the processing unit may generate a signal to indicate to a user that the treatment plan needs to be adjusted. Alternatively, or additionally, the processing unit may also adjust the treatment plan based on the image frames 212 from the first movie 210a, image frames 212 from the second movie 210b, or both.

In the above embodiments, the selection of an image frame 212 from the two-dimensional movie 210 may be performed by the processing unit in an arbitrary manner. In other embodiments, for a certain breathing phase range (e.g., P2), the processing unit may be configured to select the first image frame 212 (image frame 212f in the example) for registration with the corresponding three-dimensional image (the three-dimensional image 200b in the example). In further embodiments, for a certain breathing phase range (e.g., P2), the processing unit may be configured to select one of the image frames 212 that has an associated breathing phase closest to that associated with the three-dimensional image (e.g., the three-dimensional image 200b). For example, the phase bin for breathing phase P2 has multiple image frames 212f-212h. Accordingly, the processing unit may select one of the image frames 212f-212h associated with the breathing phase range P2 for registration with the three-dimensional image 200b that is also associated with the same breathing phase range P2. In one implementation, the processing unit is configured to select one of the image frames 212f-212h with an associated breathing phase that is the closest to a breathing phase associated with the three-dimensional images. In particular, even though image frames 212f-212h are all associated with the breathing phase range P2, they all have respective breathing phases that are different from each other since they are generated while the patient is undergoing different breathing phases. For example, breathing phase range P2 may cover a breathing phase range from 90°-180°. Accordingly, if the image frames 212f-212h from the movie 210a are generated at breathing phases of 95°, 125°, 156°, respectively for examples, then these image frames 212f-212h will be associated with the breathing phase range P2, but they will still have different respective associated breathing phases. In the illustrated embodiments, for the purpose of image registration, the processing unit may select one of these image frames 212f-212h for association or registration with the corresponding three-dimensional image 200b. In one implementation, if the corresponding three-dimensional image 200b has an associated breathing phase of 135° (which is the average of the phase range 90°-180° covered by the phase range P2) for example, the image registration module may then select image frame 212f that has the closest breathing phase (125° in the above example) for registration with the three-dimensional image 200b. In other implementation, the image registration module may pick the middle or average one for registration with the three-dimensional image.

Figure 5:
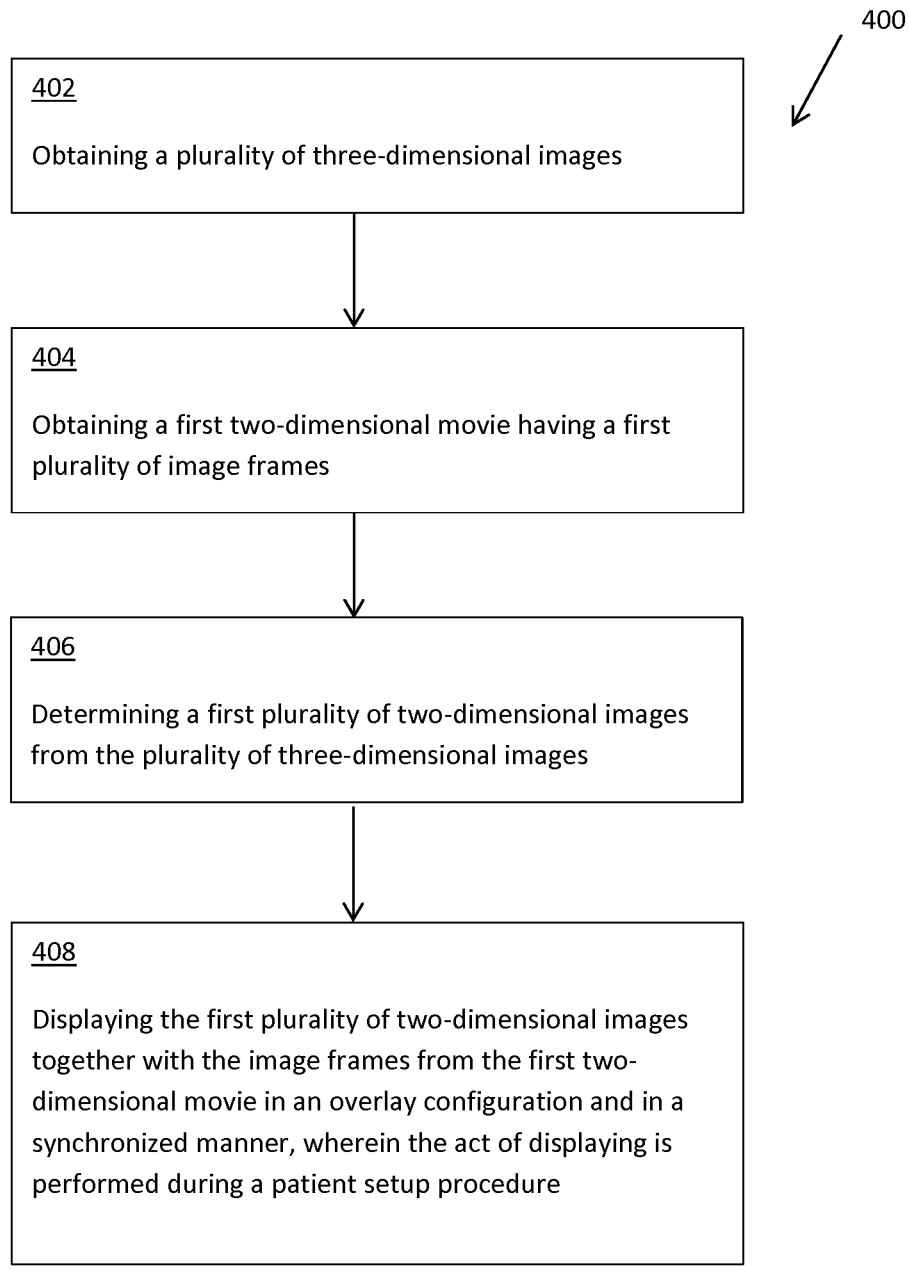
FIG. 5 illustrates a method for patient setup in accordance with some embodiments.

FIG. 5 illustrates a method 400 for patient setup in accordance with some embodiments. In some embodiments, the method 400 may be performed by a processing unit. By means of non-limiting examples, the processing unit may be the processing unit 54, or another processing unit. Also, the processing unit may be implemented using one or more processors, such as a FPGA processor, an ASIC processor, a microprocessor, a signal processor, a general purpose processor, or any of other types of processor. In some cases, the processing unit may be considered an improved processing unit compared to known processing units because the processing unit described herein contains features, functions, and/or capabilities that are believed to be unavailable in known processing units.

First, a plurality of three-dimensional images 200 are obtained (item 402). In some embodiments, the three-dimensional images 200 are volumetric CT images that are generated for treatment planning. The three-dimensional images 200 may be arranged in a sequence so that they form a video/movie. Also, in some embodiments, the three-dimensional images 200 are associated with different respective breathing phase ranges P of a respiratory cycle. For example, in some embodiments, the respiratory cycle may be divided in four phase ranges P1-P4, and the plurality of three-dimensional images 200 may include four volumetric CT images 200a-200d for the four respective phase ranges P1-P4. In other examples, the number of phase ranges may be more or fewer than four. In the illustrated embodiments, the act of obtaining the three-dimensional images 200 may be performed by the processing unit, which accesses a storage medium storing the three-dimensional images 200.

Next, the processing unit obtains a first two-dimensional movie 210a having a first plurality of image frames 212 (item 404). In the illustrated embodiments, the image frames 212 in the first two-dimensional movie 210a are fluoroscopic images generated using the first imaging system 150. The fluoroscopic images are generated in a sequence during a patient setup procedure (i.e., while the patient is on the patient support, but before treatment radiation is delivered to the patient to treat the patient).

In one implementation, the processing unit may include one or more input for obtaining the three-dimensional images 200 and the two-dimensional movie 210.

Next, the processing unit determines a first plurality of two-dimensional images 300 from the plurality of three-dimensional images 300 (item 406). In the illustrated embodiments, a two-step approach is utilized to determine the plurality of two-dimensional images 300, in which respiratory synchronization is performed, followed by geometrical registration.

In some cases, the three-dimensional images 200 are already binned, during treatment planning, into a first number of phase bins based on breathing signals obtained from a breathing monitoring device. In such cases, to perform respiratory synchronization, the processing unit may include a binning module that bins the first plurality of image frames 212 in the first two-dimensional movie 210a into a second number of phase bins, the first number being equal to the second number. As a result, the three-dimensional images 200 and the image frames 212 from the first two-dimensional movie 210a are synchronized to a common time frame based on breathing signals provided from a breathing monitoring device.

In some embodiments, when the three-dimensional images 300 are generated in the treatment planning phase, the breathing pattern of the patient may be recorded as breathing signals using a breathing monitoring device. Thus the three-dimensional images 300 may be associated with respective breathing phase ranges of a respiratory cycle of the patient. For example, three-dimensional image 200a may be associated with breathing phase range P1, three-dimensional image 200b may be associated with breathing phase range P2, three-dimensional image 200c may be associated with breathing phase range P3, and three-dimensional image 200d may be associated with breathing phase range P4. Later on, when the patient is being setup during the treatment procedure, when the two-dimensional movie 210a is being generated, the breathing phase of the patient is again determined. Following the above example, if the breathing phase during the patient setup is determined to be in the phase range P2 while image frames 212f-212h in the two-dimensional movie 210a are generated, then the binning module may associate the image frames 212f-212h with the breathing phase range P2. This way, through the breathing phase as determined from the breathing signals, certain one of the three-dimensional images 200 may be associated with certain one(s) of the image frames 212 in the two-dimensional movie 210a.

After the two-dimensional image frames 212 from the two-dimensional movie 210a has been respiratory synchronized with the three-dimensional images 300, one of the image frames 212 may be selected for geometrical registration with a corresponding one the three-dimensional images 200.

In the above example, the phase bin for breathing phase range P2 has multiple image frames 212f-212h. Accordingly, the method 400 may further include selecting one of the image frames 212f-212h from the phase bin for registration with the corresponding three-dimensional image 200 that is also associated with the same breathing phase range P2. In one implementation, the processing unit may include a two-dimensional image determination module configured to select one of the image frames 212f-212h with an associated breathing phase that is closer to a breathing phase associated with the corresponding three-dimensional image 200 compared to other ones of the image frames 212f-212h in the phase bin. In particular, even though image frames 212f-

212*h* are all associated with the breathing phase range P2, they all have respective breathing phases that are different from each other since they are generated while the patient is undergoing different breathing phases. For example, breathing phase range P2 may cover a breathing phase range from 90°-180°. Accordingly, if the image frames 212*f*-212*h* are generated at breathing phases of 95°, 125°, 156°, respectively for examples, then these image frames 212*f*-212*h* will be associated with the breathing phase range P2, but they will still have different respective associated breathing phases. In the illustrated embodiments, for the purpose of geometrical registration, the two-dimensional image determination module may select one of these image frames 212*f*-212*h* for association or registration with the corresponding three-dimensional image 200*b*. In one implementation, if the corresponding three-dimensional image 200*b* has an associated breathing phase of 135° for example, the image registration module may then select image frame 212*g* that has the closest breathing phase (156° in the above example) for registration with the three-dimensional image 200*b*. In other implementation, the two-dimensional image determination module may pick the middle or average one for registration with the three-dimensional image 200*b*. In further embodiments, the two-dimensional image determination module may pick the first image frame 212 (image frame 212*f* in the example) for the phase range P2 for geometrical registration with the corresponding three-dimensional image 200*b*.

In some embodiments, to perform geometrical registration, the two-dimensional image determination module may then determine a cross-section of the three-dimensional image 200*b* that matches the selected two-dimensional image frame 212 from the movie 210*a*. From the match, a first registration R that registers the image frames 212 in the first two-dimensional movie 210*a* with the cross section 300 in the three-dimensional image 200*b* is obtained. In some cases, the registration R may be a transformation matrix that links the image frame 212 with a cross section 300 of the three-dimensional image 200*b* that matches the image frame 212.

Also, in some embodiments, the act of determining the plurality of two-dimensional images 300 may further include: applying the first registration R, by the two-dimensional determination module, for an other one of the image frames 212 in the first two-dimensional movie 210*a*, in order to determine a corresponding two-dimensional image 300 from a corresponding three-dimensional image 200; wherein the one of the image frames 212 is associated with a first phase of a respiratory cycle, the other one of the image frames 212 is associated with a second phase of the respiratory cycle, the first phase being different from the second phase.

In other embodiments, the act of determining the plurality of two-dimensional images 300 may include: determining, by the two-dimensional image determination module, a second registration R that registers an other one of the image frames 212 in the first two-dimensional movie 210*a* with another one of the three-dimensional images 300; wherein the one of the image frames 212 is associated with a first phase of a respiratory cycle, the other one of the image frames 212 is associated with a second phase of the respiratory cycle, the first phase being different from the second phase.

Referring again to FIG. 5, next, the first plurality of two-dimensional images together with the image frames from the first two-dimensional movie are displayed in an overlay configuration and in a synchronized manner, wherein the act of displaying is performed during a patient setup procedure (item 408). In one implementation, the processing unit includes a synchronization display module configured to output the first plurality of two-dimensional images and the image frames from the first two-dimensional movie for display in an overlay configuration and in a synchronized manner.

In the above embodiments, the method 400 is described as involving a first two-dimensional movie. In other embodiments, the method 400 may involve one or more additional two-dimensional movies. For example, in some embodiments, the method 400 may further include obtaining a second two-dimensional movie 210*b* having a second plurality of image frames 212. The image frames 212 in the second two-dimensional movie 210*b* may be fluoroscopic images generated using the second imaging system 160. The fluoroscopic images are generated in a sequence during a patient setup procedure (i.e., while the patient is on the patient support, but before treatment radiation is delivered to the patient to treat the patient). In such cases, the method 400 may further include determining a second plurality of two-dimensional images 300 from the plurality of three-dimensional images 200, and displaying the second plurality of two-dimensional images 300 together with the image frames 212 from the second two-dimensional movie 210*b* in an overlay configuration and in a synchronized manner.

In the above embodiments, the first plurality of image frames 212 in the first two-dimensional movie 210*a* comprises a first set of fluoroscopic images, and the second plurality of image frames 212 in the second two-dimensional movie 210*b* comprises a second set of fluoroscopic images. In some cases, the first set of fluoroscopic images comprises kV images, and the second set of fluoroscopic images comprises MV images. In other cases, the first set of fluoroscopic images comprises a first set of kV images, and the second set of fluoroscopic images comprises a second set of kV images. In further cases, the first set of fluoroscopic images may include a first set of MV images, and the second set of fluoroscopic images may include a second set of MV images. In still further cases, the first set of fluoroscopic images may include kV images or MV images, and the second set of fluoroscopic images may include magnetic resonance images, or vice versa.

In some embodiments, the first two-dimensional movie 210*a* is generated using x-ray. For example, the x-ray for generating the first two-dimensional movie 210*a* may comprise kV x-ray. Alternatively, the x-ray for generating the first two-dimensional movie 210*a* may comprise MV x-ray. In other embodiments, the first two-dimensional movie 210*a* may be generated using ultrasound. In further embodiments, the first two-dimensional movie 210*a* may be generated using other imaging techniques.

Also, the three dimensional images 200 may comprise CBCT images, magnetic resonance images, CT images, or positron emission tomography (PET) images.

In some embodiments, the first plurality of two-dimensional images 300 has a first frame rate, the first two-dimensional movie 210*a* has a second frame rate, the first frame rate being different from the second frame rate. In other embodiments, the first frame rate may be the same as the second frame rate.

Figure 6:
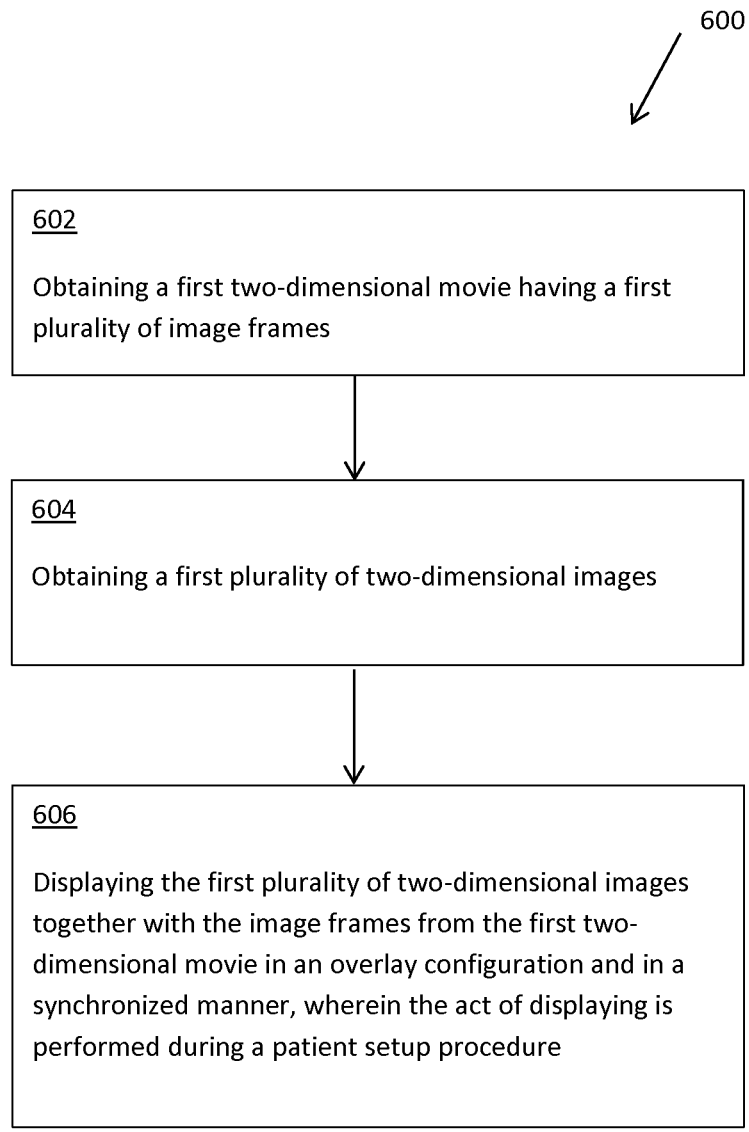
FIG. 6 illustrates another method for patient setup in accordance with some embodiments.

In the above embodiments, the two-dimensional images for registration with the image frames from the two-dimensional movie are obtained as cross sections from a plurality of three-dimensional images. In other embodiments, the two-dimensional images for registration with the image frames from the two-dimensional movie may be raw projection images, or any of other types of images that are not derived from three-dimensional images. Accordingly, the method 400 may be generalized for other types of two-dimensional images for registration with the image frames from the two-dimensional movie. FIG. 6 illustrates a method 600 for patient setup in accordance with some embodiments. In some embodiments, the method 600 may be performed by a processing unit. By means of non-limiting examples, the processing unit may be the processing unit 54, or another processing unit. Also, the processing unit may be implemented using one or more processors, such as a FPGA processor, an ASIC processor, a microprocessor, a signal processor, a general purpose processor, or any of other types of processor. In some cases, the processing unit may be considered an improved processing unit compared to known processing units because the processing unit described herein contains features, functions, and/or capabilities that are believed to be unavailable in known processing units.

The method 600 is similar to the method 400, except that the two-dimensional images for registration with the image frames from the movie is not limited to sectional images derived from three-dimensional images. First, the processing unit obtains a first two-dimensional movie having a first plurality of image frames (item 602). Item 602 is similar to item 404 described previously with reference to the method 400.

Next, the processing unit obtains a first plurality of two-dimensional images (item 604). In some embodiments, the two-dimensional images comprise a first plurality of projection images. For example, the projection images may be raw projection images of a CT (e.g., CBCT) data set. In other embodiments, the two-dimensional images are two-dimensional sections of respective three-dimensional images.

Next, the first plurality of two-dimensional images and the image frames from the first two-dimensional movie are displayed together in an overlay configuration and in a synchronized manner, wherein the act of displaying is performed during a patient setup procedure (item 606). Item 606 is similar to item 408 described previously with reference to the method 400.

In the above embodiments, the patient setup technique is described as involving use of breathing signals obtained from breathing monitoring device. In other embodiments, the breathing signals may not be available. In such cases, instead of the 2D/3D registration described above (i.e., registering a x-ray image frame against one respiratory phase of the 4D CT), the processing unit may be configured to perform 2D/4D registration. The additional degree of freedom in the optimization algorithm run by the processing unit would then be responsible for finding the best corresponding respiratory phase out of the 4D CT. In some cases, instead of calculating the optimal registration between a 2D movie frame and the 4D CT, the processing unit may calculate an average best match by registering each 2D movie frame with the 4D data set.

Also, it should be noted that the synchronous display of images described herein may be performed retroactively in some embodiments. In other embodiments, the synchronous display of images may be performed in real time. The synchronous display of images may be performed shortly (e.g., within 2 seconds, and more preferably within 1 second, and even more preferably within 0.5 seconds or less) after the image frame 212 in the movie 210 is generated.

Processing System Architecture

Figure 7:
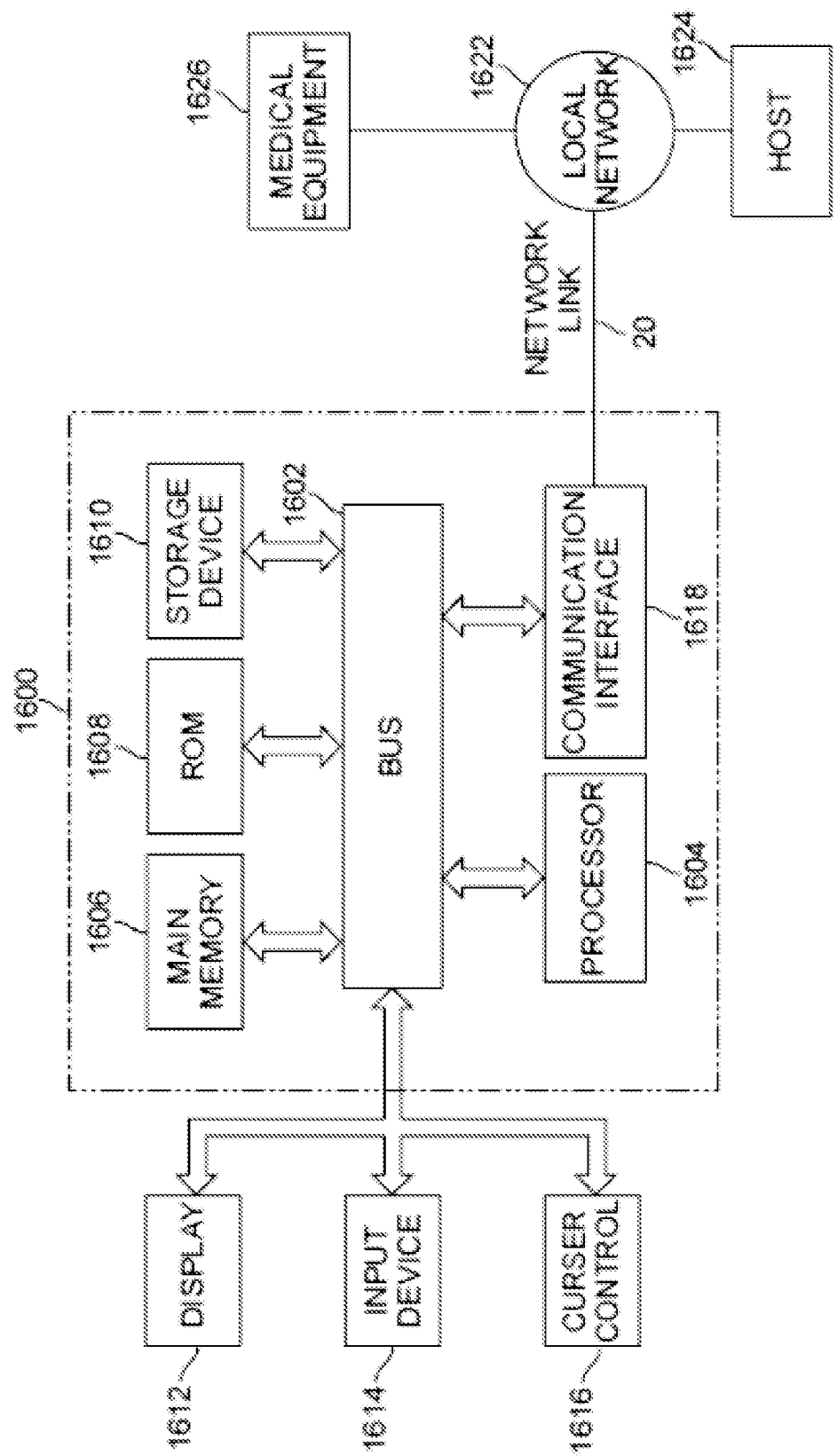
FIG. 7 illustrates a specialized processing system with which embodiments described herein may be implemented.

FIG. 7 is a block diagram illustrating an embodiment of a specialized processing system 1600 that can be used to implement various embodiments described herein. For example, the processing system 1600 may be configured to implement the method of FIG. 5/6 in accordance with some embodiments. Also, in some embodiments, the processing system 1600 may be used to implement the processing unit 54 of FIG. 1. The processing system 1600 includes a bus 1602 or other communication mechanism for communicating information, and a processor 1604 coupled with the bus 1602 for processing information. The processor 1604 may be an example of the processor 54 of FIG. 1, or an example of any processor described herein. The processing system 1600 also includes a main memory 1606, such as a random access memory (RAM) or other dynamic storage device, coupled to the bus 1602 for storing information and instructions to be executed by the processor 1604. The main memory 1606 also may be used for storing temporary variables or other intermediate information during execution of instructions to be executed by the processor 1604. The processing system 1600 further includes a read only memory (ROM) 1608 or other static storage device coupled to the bus 1602 for storing static information and instructions for the processor 1604. A data storage device 1610, such as a magnetic disk or optical disk, is provided and coupled to the bus 1602 for storing information and instructions.

The processing system 1600 may be coupled via the bus 1602 to a display 167, such as a cathode ray tube (CRT), for displaying information to a user. An input device 1614, including alphanumeric and other keys, is coupled to the bus 1602 for communicating information and command selections to processor 1604. Another type of user input device is cursor control 1616, such as a mouse, a trackball, or cursor direction keys for communicating direction information and command selections to processor 1604 and for controlling cursor movement on display 167. This input device typically has two degrees of freedom in two axes, a first axis (e.g., x) and a second axis (e.g., y), that allows the device to specify positions in a plane.

In some embodiments, the processing system 1600 can be used to perform various functions described herein. According to some embodiments, such use is provided by processing system 1600 in response to processor 1604 executing one or more sequences of one or more instructions contained in the main memory 1606. Those skilled in the art will know how to prepare such instructions based on the functions and methods described herein. Such instructions may be read into the main memory 1606 from another processor-readable medium, such as storage device 1610. Execution of the sequences of instructions contained in the main memory 1606 causes the processor 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the various embodiments described herein. Thus, embodiments are not limited to any specific combination of hardware circuitry and software.

The term "processor-readable medium" as used herein refers to any medium that participates in providing instructions to the processor 1604 for execution. Such a medium may take many forms, including but not limited to, non-volatile media, volatile media, and transmission media. Non-volatile media includes, for example, optical or magnetic disks, such as the storage device 1610. A non-volatile medium may be considered an example of non-transitory medium. Volatile media includes dynamic memory, such as the main memory 1606. A volatile medium may be considered an example of non-transitory medium. Transmission media includes coaxial cables, copper wire and fiber optics, including the wires that comprise the bus 1602. Transmission media can also take the form of acoustic or light waves, such as those generated during radio wave and infrared data communications.

Common forms of processor-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a processor can read.

Various forms of processor-readable media may be involved in carrying one or more sequences of one or more instructions to the processor 1604 for execution. For example, the instructions may initially be carried on a magnetic disk of a remote computer. The remote computer can load the instructions into its dynamic memory and send the instructions over a telephone line using a modem. A modem local to the processing system 1600 can receive the data on the telephone line and use an infrared transmitter to convert the data to an infrared signal. An infrared detector coupled to the bus 1602 can receive the data carried in the infrared signal and place the data on the bus 1602. The bus 1602 carries the data to the main memory 1606, from which the processor 1604 retrieves and executes the instructions. The instructions received by the main memory 1606 may optionally be stored on the storage device 1610 either before or after execution by the processor 1604.

The processing system 1600 also includes a communication interface 1618 coupled to the bus 1602. The communication interface 1618 provides a two-way data communication coupling to a network link 1620 that is connected to a local network 1622. For example, the communication interface 1618 may be an integrated services digital network (ISDN) card or a modem to provide a data communication connection to a corresponding type of telephone line. As another example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626 such as a radiation beam source or a switch operatively coupled to a radiation beam source. The data streams transported over the network link 1620 can comprise electrical, electromagnetic or optical signals. The signals through the various networks and the signals on the network link 1620 and through the communication interface 1618, which carry data to and from the processing system 1600, are exemplary forms of carrier waves transporting the information. The processing system 1600 can send messages and receive data, including program code, through the network(s), the network link 1620, and the communication interface 1618.

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents.

The invention claimed is:

1. A method for patient setup, comprising:
    obtaining a plurality of three-dimensional images of a four-dimensional (4D) sequence;
    obtaining a first two-dimensional movie having a first plurality of image frames;
    determining a first plurality of two-dimensional images from the plurality of three-dimensional images; and
    displaying the first plurality of two-dimensional images determined from the plurality of three-dimensional images of the 4D sequence together with the image frames from the first two-dimensional movie in an overlay configuration in a synchronized manner, wherein the act of displaying is performed during a patient setup procedure, and wherein the first plurality of the two-dimensional images determined from the plurality of three-dimensional images of the 4D sequence and the image frames that are displayed in an overlay configuration together form a video;
    wherein the act of displaying is performed by (a) displaying a first edge of a first internal anatomical feature in one of the first plurality of two-dimensional images, and a second edge of a second internal anatomical feature in one of the image frames, in an overlay manner with respect to each other, to show a relative displacement between the first edge and the second edge, and (b) repeating (a) for another one of the first plurality of two-dimensional images and for another one of the image frames to show a change in the relative displacement over time.

2. The method of claim 1, further comprising:
    obtaining a second two-dimensional movie having a second plurality of image frames;
    determining a second plurality of two-dimensional images from the plurality of three-dimensional images; and
    displaying the second plurality of two-dimensional images together with the image frames from the second two-dimensional movie in an overlay configuration and in a synchronized manner.

3. The method of claim 2, wherein the first plurality of image frames in the first two-dimensional movie comprises a first set of fluoroscopic images, and the second plurality of image frames in the second two-dimensional movie comprises a second set of fluoroscopic images.

4. The method of claim 3, wherein the first set of fluoroscopic images comprises kV images, and the second set of fluoroscopic images comprises MV images.

5. The method of claim 3, wherein the first set of fluoroscopic images comprises a first set of kV or MV images, and the second set of fluoroscopic images comprises a second set of kV or MV images.

6. The method of claim 1, wherein the act of determining the plurality of two-dimensional images comprises:
    determining a cross section in one of the plurality of three-dimensional images that matches with one of the image frames in the first two-dimensional movie, wherein the match results in a first registration.

7. The method of claim 6, wherein the act of determining the plurality of two-dimensional images further comprises:
    applying the first registration for an other one of the image frames in the first two-dimensional movie;

wherein the one of the image frames is associated with a first phase of a respiratory cycle, the other one of the image frames is associated with a second phase of the respiratory cycle, the first phase being different from the second phase.

8. The method of claim 6, wherein the act of determining the plurality of two-dimensional images comprises:
determining an other cross section in an other one of the plurality of three-dimensional images that matches with an other one of the image frames in the first two-dimensional movie,
wherein the one of the image frames is associated with a first phase of a respiratory cycle, the other one of the image frames is associated with a second phase of the respiratory cycle, the first phase being different from the second phase.

9. The method of claim 1, the first plurality of two-dimensional images and the image frames from the first two-dimensional movie are synchronized to a common time frame based on breathing signals provided from a breathing monitoring device.

10. The method of claim 1, wherein the plurality of three-dimensional images are binned into a first number of phase bins, and wherein the method further comprises binning the first plurality of image frames in the first two-dimensional movie into a second number of phase bins, the first number being equal to the second number.

11. The method of claim 10, wherein a phase bin in the second number of phase bins has multiple images from the first plurality of image frames, and wherein the method further comprises selecting one of the images from the phase bin in the second number of the phase bins for registration with one of the plurality of three-dimensional images.

12. The method of claim 11, wherein the selected one of the images has an associated breathing phase that is closer to a breathing phase associated with the one of the plurality of three-dimensional images compared to other ones of the images.

13. The method of claim 1, wherein the first two-dimensional movie is generated using x-ray.

14. The method of claim 13, wherein the x-ray comprises kV x-ray.

15. The method of claim 13, wherein the x-ray comprises MV x-ray.

16. The method of claim 1, wherein the first two-dimensional movie is generated using ultrasound or magnetic resonance.

17. The method of claim 1, wherein the three dimensional images comprise CBCT images, magnetic resonance images, CT images, or PET images.

18. The method of claim 1, wherein the first plurality of two-dimensional images has a first frame rate, the first two-dimensional movie has a second frame rate, the first frame rate being different from the second frame rate.

19. The method of claim 1, wherein the overlay configuration indicates whether a target is at a desired position for receiving treatment radiation.

20. The method of claim 1, wherein the video has respective features from the first plurality of the two-dimensional images and the first plurality of image frames that are synchronized based on breathing data.

21. The method of claim 1, wherein the video comprises a sequence of video frames, wherein each video frame comprises overlaid images.

22. An apparatus for patient setup, comprising:
a processing unit having one or more input for obtaining a plurality of three-dimensional images of a four-dimensional (4D) sequence, and for obtaining a first two-dimensional movie having a first plurality of image frames;
wherein the processing unit comprises a two-dimensional image determination module configured for determining a first plurality of two-dimensional images from the plurality of three-dimensional images of the four-dimensional (4D) sequence;
wherein the processing unit further comprises a synchronization display module configured to output (1) the first plurality of two-dimensional images determined from the plurality of three-dimensional images of the 4D sequence and (2) the image frames from the first two-dimensional movie for display together in an overlay configuration and in a synchronized manner in a patient setup procedure, and wherein the first plurality of the two-dimensional images determined from the plurality of three-dimensional images of the 4D sequence and the image frames that are displayed in an overlay configuration together form a video; and
wherein the synchronization display module is configured to (a) display a first edge of a first internal anatomical feature in one of the first plurality of two-dimensional images, and a second edge of a second internal anatomical feature in one of the image frames, in an overlay manner with respect to each other, to show a relative displacement between the first edge and the second edge, and (b) repeat (a) for another one of the first plurality of two-dimensional images and for another one of the image frames to show a change in the relative displacement over time.

23. The apparatus of claim 22, wherein the one or more input of the processing unit is configured for obtaining a second two-dimensional movie having a second plurality of image frames;
wherein the two-dimensional image determination module is configured for determining a second plurality of two-dimensional images from the plurality of three-dimensional images; and
wherein the synchronization display module is configured for displaying the second plurality of two-dimensional images together with the image frames from the second two-dimensional movie in an overlay configuration and in a synchronized manner.

24. The apparatus of claim 23, wherein the first plurality of image frames in the first two-dimensional movie comprises a first set of fluoroscopic images, and the second plurality of image frames in the second two-dimensional movie comprises a second set of fluoroscopic images.

25. The apparatus of claim 24, wherein the first set of fluoroscopic images comprises kV images, and the second set of fluoroscopic images comprises MV images.

26. The apparatus of claim 24, wherein the first set of fluoroscopic images comprises a first set of kV or MV images, and the second set of fluoroscopic images comprises a second set of kV or MV images.

27. The apparatus of claim 22, wherein the two-dimensional image determination module is configured for determining a cross section in one of the plurality of three-dimensional images that matches with one of the image frames in the first two-dimensional movie, wherein the match results in a first registration.

28. The apparatus of claim 27, wherein the two-dimensional image determination module is configured for applying the first registration for an other one of the image frames in the first two-dimensional movie;

wherein the one of the image frames is associated with a first phase of a respiratory cycle, the other one of the image frames is associated with a second phase of the respiratory cycle, the first phase being different from the second phase.

29. The apparatus of claim 27, wherein the two-dimensional image determination module is configured for determining an other cross section in an other one of the plurality of three-dimensional images that matches with an other one of the image frames in the first two-dimensional movie; wherein the one of the image frames is associated with a first phase of a respiratory cycle, the other one of the image frames is associated with a second phase of the respiratory cycle, the first phase being different from the second phase.

30. The apparatus of claim 22, wherein the processing unit is also configured to obtain breathing signals generated using a breathing monitoring device, and wherein the synchronization display module is configured to synchronize the first plurality of two-dimensional images and the image frames from the first two-dimensional movie to a common time frame based on the breathing signals.

31. The apparatus of claim 22, wherein the plurality of three-dimensional images are binned into a first number of phase bins, and wherein the processing unit comprises a binning module configured to bin the first plurality of image frames in the first two-dimensional movie into a second number of phase bins, the first number being equal to the second number.

32. The apparatus of claim 31, wherein a phase bin in the second number of phase bins has multiple images from the first plurality of image frames, and wherein the two-dimensional image determination module is configured for selecting one of the images from the phase bin in the second number of phase bins for registration with one of the plurality of three-dimensional images.

33. The apparatus of claim 32, wherein the selected one of the images has an associated breathing phase that is closer to a breathing phase associated with the one of the plurality of three-dimensional images compared to other ones of the images.

34. The apparatus of claim 22, wherein the first two-dimensional movie is generated using x-ray.

35. The apparatus of claim 34, wherein the x-ray comprises kV x-ray.

36. The apparatus of claim 34, wherein the x-ray comprises MV x-ray.

37. The apparatus of claim 22, wherein the first two-dimensional movie is generated using ultrasound or magnetic field.

38. The apparatus of claim 22, wherein the three dimensional images comprise CBCT images, magnetic resonance images, CT images, or PET images.

39. The apparatus of claim 22, wherein the first plurality of two-dimensional images has a first frame rate, the first two-dimensional movie has a second frame rate, the first frame rate being different from the second frame rate.

40. The apparatus of claim 22, wherein the overlay configuration indicates whether a target is at a desired position for receiving treatment radiation.

41. The apparatus of claim 22, wherein the video has respective features from the first plurality of the two-dimensional images and the image frames that are synchronized based on breathing data.

42. A processor-program product having a set of instruction, an execution of which by a processing unit causes a method of detecting camera defect to be performed, the method comprising:
obtaining a plurality of three-dimensional images of a four-dimensional (4D) sequence;
obtaining a first two-dimensional movie having a first plurality of image frames;
determining a first plurality of two-dimensional images from the plurality of three-dimensional images of the 4D sequence; and
displaying the first plurality of two-dimensional images determined from the plurality of three-dimensional images of the 4D sequence together with the image frames from the first two-dimensional movie in an overlay configuration and in a synchronized manner, wherein the act of displaying is performed during a patient setup procedure, and wherein the first plurality of the two-dimensional images determined from the plurality of three-dimensional images of the 4D sequence and the image frames that are displayed in an overlay configuration together form a video;
wherein the act of displaying is performed by (a) displaying a first edge of a first internal anatomical feature in one of the first plurality of two-dimensional images, and a second edge of a second internal anatomical feature in one of the image frames, in an overlay manner with respect to each other, to show a relative displacement between the first edge and the second edge, and (b) repeating (a) for another one of the first plurality of two-dimensional images and for another one of the image frames to show a change in the relative displacement over time.

43. A method for patient setup, comprising:
obtaining a first two-dimensional movie having a first plurality of image frames;
obtaining a first plurality of two-dimensional images that collectively form a video stream; and
displaying the first plurality of two-dimensional images together with the image frames from the first two-dimensional movie in an overlay configuration and in a synchronized manner, wherein the act of displaying is performed during a patient setup procedure, and wherein the first plurality of the two-dimensional images of the video stream and the image frames that are displayed in an overlay configuration together form a video;
wherein the act of displaying is performed by (a) displaying a first edge of a first internal anatomical feature in one of the first plurality of two-dimensional images, and a second edge of a second internal anatomical feature in one of the image frames, in an overlay manner with respect to each other, to show a relative displacement between the first edge and the second edge, and (b) repeating (a) for another one of the first plurality of two-dimensional images and for another one of the image frames to show a change in the relative displacement over time.

44. The method of claim 43, wherein the two-dimensional images are two-dimensional sections of respective three-dimensional images.

45. The method of claim 43, wherein the first plurality of two-dimensional images comprises a first plurality of projection images.

46. The method of claim 43, wherein the video has respective features from the first plurality of the two-dimensional images and the image frames that are synchronized based on breathing data.

47. The method of claim 43, wherein the video comprises a sequence of video frames, wherein each video frame comprises overlaid images.

48. An apparatus for patient setup, comprising:
a processing unit configured to obtain a first two-dimensional movie having a first plurality of image frames, and to obtain a first plurality of two-dimensional images that collectively form a video stream;
wherein the processing unit comprises a synchronization display module configured to output the first plurality of two-dimensional images and with the image frames from the first two-dimensional movie for display in an overlay configuration and in a synchronized manner in a patient setup procedure, and wherein the first plurality of the two-dimensional images of the video stream and the image frames that are displayed in an overlay configuration together form a video; and
wherein the synchronization display module is configured to (a) display a first edge of a first internal anatomical feature in one of the first plurality of two-dimensional images, and a second edge of a second internal anatomical feature in one of the image frames, in an overlay manner with respect to each other, to show a relative displacement between the first edge and the second edge, and (b) repeat (a) for another one of the first plurality of two-dimensional images and for another one of the image frames to show a change in the relative displacement over time.

49. The apparatus of claim 48, wherein the two-dimensional images are two-dimensional sections of respective three-dimensional images.

50. The apparatus of claim 48, wherein the first plurality of two-dimensional images comprises a first plurality of projection images.

51. The apparatus of claim 48, wherein the video has respective features from the first plurality of the two-dimensional images and the image frames that are synchronized based on breathing data.

52. A processor-program product having a set of instruction, an execution of which by a processing unit causes a method of detecting camera defect to be performed, the method comprising:
obtaining a first two-dimensional movie having a first plurality of image frames;
obtaining a first plurality of two-dimensional images that collectively form a video stream; and
displaying the first plurality of two-dimensional images together with the image frames from the first two-dimensional movie in an overlay configuration and in a synchronized manner, wherein the act of displaying is performed during a patient setup procedure, and wherein the first plurality of the two-dimensional images of the video stream and the image frames that are displayed in an overlay configuration together form a video;
wherein the act of displaying is performed by (a) displaying a first edge of a first internal anatomical feature in one of the first plurality of two-dimensional images, and a second edge of a second internal anatomical feature in one of the image frames, in an overlay manner with respect to each other, to show a relative displacement between the first edge and the second edge, and (b) repeating (a) for another one of the first plurality of two-dimensional images and for another one of the image frames to show a change in the relative displacement over time.

* * * * *